(12) United States Patent
Brown

(10) Patent No.: US 6,284,805 B1
(45) Date of Patent: Sep. 4, 2001

(54) PLASTICS CONTAINER CONTAINING STABILIZED DRUG FORMULATION

(75) Inventor: Stephen Brown, Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/433,158

(22) Filed: Nov. 3, 1999

(30) Foreign Application Priority Data

Nov. 4, 1998 (GB) .................................................. 9824161

(51) Int. Cl.$^7$ .................................................. A61K 31/445
(52) U.S. Cl. ............................................ 514/818; 514/330
(58) Field of Search .................................. 514/330, 818; 424/78, 78.02, 451, 677, 715

(56) References Cited

U.S. PATENT DOCUMENTS

| | | | |
|---|---|---|---|
| 4,474,751 | * | 10/1984 | Haslam et al. ........................ 424/78 |
| 5,505,922 | * | 4/1996 | Thut et al. ........................... 424/677 |
| 5,736,127 | * | 4/1998 | Stoy et al. .......................... 424/78.02 |
| 5,932,597 | * | 8/1999 | Brown ................................. 514/330 |

OTHER PUBLICATIONS

Jones, Jerry W. et al. (1993) "Stability of bupivacaine hydrochloride in polypropylene syringes" *Am J Hosp Pharm* 50:2364–2365.

Upton, Richard N. et al. (1987) "The Relationship Between Some Physicochemical Properties of Ionisable Drugs and their Sorption into Medical Plastics" *Aust J Hosp Pharm* 17(4):267–270.

Da Poiam, Sergio Hampe et al. (1983) "Adrenalina, Esterilizacao, pH e Dissociacao dos Anestesicos Locais" *Revista Brasileira de Anestesiologia* 33(1):23–25.

Liang, Jin et al. (1982) "Preparation of bupivacaine injection and its physicochemical properties" *Chem. Abs.* 97(25):222883.

* cited by examiner

Primary Examiner—Thurman K. Page
Assistant Examiner—Blessing Fubara
(74) *Attorney, Agent, or Firm*—Saliwanchik, Lloyd & Saliwanchik

(57) ABSTRACT

A plastics container containing a sterile aqueous solution of an acid addition salt of a 1-alkyl-N-(2,6-dimethylphenyl)-2-piperidinecaboxamide, wherein the solution is buffered.

12 Claims, No Drawings

US 6,284,805 B1

PLASTICS CONTAINER CONTAINING STABILIZED DRUG FORMULATION

FIELD OF THE INVENTION

This invention relates to a new drug formulation, and in particular to bags, ampoules or other containers including a sterile drug solution.

BACKGROUND OF THE INVENTION

Many drugs are provided in aqueous solution. For this purpose, they are typically packaged, in a glass, plastics or other container such as an ampoule, vial or bag, and sterilised by autoclaving. They can then be stored and used as necessary.

One class of drugs that is administered as a solution, e.g. by injection or infusion, comprises the long-acting local anesthetics which include an amine. Particular examples of this type of therapeutic agent are 1-alkyl-N-(2,6-dimethylphenyl)-2-piperidinecarboxamides, of which specific examples are mepivacaine, ropivacaine, bupivacaine and levobupivacaine. These drugs are usually provided as the hydrochloride salt.

Jones et al, Am. J. Hosp. Path. 50(11):2364–5 (1993), reports that there were no significant changes in assay or pH upon storage of bupivacaine in polypropylene syringes.

Similarly, Upton etat, Aus. J. Hosp. Pharm. 17(4): 267–70 (1987), demonstrated no adsorption of bupivacaine to a range of plastics inducing polypropylene.

Hampe Da Poian et al, Revista Brasileira de Anestesiologia 33(1):23–5 (1983), reported no significant changes in pH or stability of solutions of bupivacaine (0.25%, 0.5%, 0.75%) following sterilisation in glass ampoules.

Chem. Abs. 97(25):222883 (1982) indicates that solutions of bupivacaine in vials were stable to heat and light following sterilisation.

U.S. Pat. No. 5,505,922 discloses a combination of a local anesthetic and lithium ions, to provide enhanced anesthetic activity. The lithium ions are described as a buffer. Among various possible additional components, it is suggested that pH buffers may be used to establish a physiologically compatible pH range and to enhance the solubility of the anesthetic.

SUMMARY OF THE INVENTION

The present invention is based on the identification of a problem associated with the provision of sterile aqueous solutions of an acid addition salt of such carboxamide therapeutic agents, in a plastics container, on the discovery of a reason for this problem, and also on a solution to it. The problem is that autoclaving causes a reduction in pH, and this may make the formulation more acidic than is suitable for the intended use, particularly if a narrow pH range has been specified, for regulatory purposes. As shown by the evidence presented below, the problem is caused by adsorption of the free base by the plastics, with the release of acid. This problem is solved by the use of a buffer.

DESCRIPTION OF THE INVENTION

The problem that is addressed by the present invention has been observed, and will be described with reference to these materials by way of illustration only, when the material of the container is polypropylene and the therapeutic agent is levobupivacaine hydrochloride salt. Polypropylene is often preferred for use in ampoules, vials or bags, e.g. of the type intended for infusion, but the invention may be equally applicable to other plastics materials, including other polyolefin polymers and copolymers.

The pKa of levobupivacaine is about 8.2 at 25° C. Typically, a solution of levobupivacaine.HCl has a pH of 5–5.5. On autoclaving in polypropylene ampoules, a pH drop is observed. It has been found that a small amount (about 1%) of free base is adsorbed by the polypropylene during the autoclave cycle of an unbuffered solution, and that adsorption in buffered solutions increases with pH. Thus, for example, buffer strength from 5 to 250 mM at pH 6 gives 30–40% adsorption, while buffering at 10 mM, pH 4, gave no pH change and limitation adsorption to 0.2%.

The theory behind these observations is that the pKa of the amine group in levobupivacaine drops as the temperature increases during the autoclaving cycle, providing free base in solution The hydrophobic free base is adsorbed by the polypropylene, leaving residual HCl in solution, causing reduction of the pH. This reduction itself causes reprotonation of the remaining free base in solution, limiting the adsorption. In buffered systems of sufficient strength, the acid is removed by the buffer, and the pH is maintained; in turn, this gives a constant salt:free base ratio. This ratio will be of the order of 100:1 at 2 pH limit below the pKa, and may be of the order of 50:50 at a pH equal to the pKa. This ratio determines the amount of adsorption.

For the carboxamide-type anesthetic agents that are used in this invention, especial benefit may be seen when its concentration in solution is relatively high, e.g. at least 0.75% w/v. At such a concentration, the pH drop observed on autoclaving is relatively great. However, a desire effect may be seen at lower concentrations, e.g. 0.25 or 0.5% w/w.

Any suitable buffer may be used, and in particular a salt formed between a weak acid and a strong base. Typical examples of such buffers are alkaline metal citrates, lactates and acetates. The amount of buffer that is required can be very small, e.g. 5 to 100 mM.

Typically, the acid forming the acid addition salt of the carboamide is different from that forming the buffer. It is preferably a hydrohalide salt, and most preferably the hydrochloride.

The present invention is based on the following experimental evidence.

EXPERIMENTS

Levobupivacaine.HCl solutions in water for injection have a natural pH of 5.0–5.5. Autoclaving these solutions in the presence of polypropylene (PPE) causes the pH of the resulting solution to decrease by 1–2 pH units.

A test solution was prepared by dissolving 1250 mg of levobupivacaine.HCl in sodium chloride 0.5%, to provide a concentration of 2.5 mg.ml$^{-1}$. A control solution of sodium chloride 0.9% was also prepared. The pH values of both the saline and the levobupivacaine.HCl solutions were measured, and the levobupivacaine.HCl solution was analysed by HPLC to determine the concentration of levobupivacaine.HCl present Levobupivacaine.HCl solution (200 ml) was transferred into two 250 ml autoclavable Schott bottles along with 20 grams of PPE (Appryl), and the lids sealed. A control bottle containing 200 ml of sodium chloride 0.9% was also prepared in a similar manner.

The control bottle containing the saline solution and one of the bottles with the levobupivacaine.HCl solution were autoclaved at 121° C. for 20 minutes. The second bottle containing levobupivacaine.HCl was left at ambient temperature.

The pH and assay of each solution were determined after autoclaving. The pH of the solution which was autoclaved in the presence of PPE was decreased compared to the initial determination and the assay of each solution remained unchanged. This data showed that gross adsorption of levobupivacaine to PPE was not occurring during autoclaving.

In order to determine if low levels of levobupivacaine were being adsorbed to the PPE, the PPE was recovered from solution and a surface extraction process was employed. The PPE was separated from the solutions by filtration through a sintered glass funnel and then washed with 8×250 ml of HPLC grade water to remove any solution from the surface. The PPE was then dried for 65 hours in a vacuum oven, containing a tray of silica gel as a desiccant, at 70° C. Once dried, the PPE was weighed and transferred into a clean 250 ml Schott bottle. HPLC grade dichloromethane (200 ml) was added and the lid sealed. After 48 h of extraction time, the PPE was removed by filtration. The dichloromethane was transferred to a round-bottom flask and removed by rotary evaporation, and the residue was dissolved in and diluted to 10 ml with tetrahydrofuran (THF)

A standard solution of bupivacaine free base (1 mg ml$^{31}$) in THF was prepared. The level of levobupivacaine base in solution was determined by chromatography against the standard and from this the level of adsorption was calculated to be 0.97%.

These experiments show that there is interaction between polypropylene and levobupivacaine.HCl during autoclaving in aqueous solution. Levobupivacaine adsorbs on to the plastic to a small extent as the free base, which leaves a slight excess of HCl in solution. This is manifested as a decrease in pH.

What is claimed is:

1. A plastic container containing a sterile aqueous solution of an acid addition salt of a 1-alkyl-N-(2,6-dimethylphenyl)-2-piperidinecarboxamide, wherein the solution is buffered to pH 3–6.

2. The container according to claim 1, wherein the container is an ampoule or vial.

3. The container according to claim 1, wherein the container is a bag.

4. The container according to claim 1, wherein the material of the container is polypropylene.

5. The container according to claim 1, wherein the salt is a hydrohalide.

6. The container according to claim 5, wherein the salt is the hydrochloride.

7. The container according to claim 1, wherein the carboxamide is bupivacaine or levobupivacaine.

8. The container according to claim 1, wherein the solution comprises at least 0.75% w/v of the carboxanide.

9. The container according to claim 1, wherein the solution is buffered to pH 3.5–5.

10. The container according to claim 1, wherein the buffer is citrate.

11. The container according to claim 2, wherein the material of the container is polypropylene.

12. The container according to claim 3, wherein the material of the container is polypropylene.

* * * * *

UNITED STATES PATENT AND TRADEMARK OFFICE
CERTIFICATE OF CORRECTION

PATENT NO. : 6,284,805 B1      Page 1 of 1
DATED : September 4, 2001
INVENTOR(S) : Stephen Brown It is certified that error appears in the above-identified patent and that said Letters Patent is hereby corrected as shown below:

Column 4,
Line 4, "plastic" should read -- plastics --.
Line 21, "carboxanide" should read -- carboxamide --.

Signed and Sealed this

Twelfth Day of March, 2002

Attest:

JAMES E. ROGAN
*Attesting Officer*     *Director of the United States Patent and Trademark Office*